United States Patent [19]

Janssen et al.

[11] Patent Number: 4,663,338

[45] Date of Patent: May 5, 1987

[54] TREATMENT OF VIRAL DISEASES

[75] Inventors: Bernd Janssen; Horst Koenig, both of Ludwigshafen; Peter Scharwaechter, Moorrege, all of Fed. Rep. of Germany

[73] Assignee: BASF Aktiengesellschaft, Fed. Rep. of Germany

[21] Appl. No.: 839,162

[22] Filed: Mar. 13, 1986

[30] Foreign Application Priority Data

Mar. 29, 1985 [DE] Fed. Rep. of Germany ....... 3511409

[51] Int. Cl.⁴ ............................................. A61K 31/41
[52] U.S. Cl. ................................................... 514/383
[58] Field of Search ......................................... 514/383

[56] References Cited

U.S. PATENT DOCUMENTS 4,551,469 11/1985 Parry et al. ......................... 514/383
4,564,622 1/1986 Streissle et al. ...................... 514/383

FOREIGN PATENT DOCUMENTS 1183449 3/1985 Canada ................................ 514/383
36153 9/1981 European Pat. Off. ............. 514/383

OTHER PUBLICATIONS

Burger's Medicinal Chemistry, IV Edition, 1979, Part 2, pp. 554 et seq., Editor M. E. Wolff.
Chemical Abstracts 102:95653b (1985).
Chemical Abstracts 96:20106x (1982).

*Primary Examiner*—Jerome D. Goldberg
*Attorney, Agent, or Firm*—Keil & Weinkauf

[57] ABSTRACT

Viral diseases are treated by a method in which an effective amount of 1-(4-chlorophenyl)-1-(2,4-dichlorophenyl)-2-(1,2,4-triazol-1-yl)-ethan-1-ol (formula I)

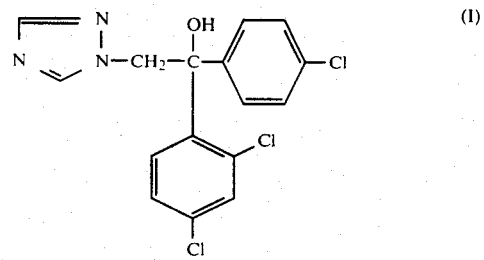

is administered enterally, parenterally or topically to a patient suffering therefrom.

1 Claim, No Drawings

TREATMENT OF VIRAL DISEASES

The present invention relates to the use of 1-(4-chlorophenyl)-1-(2,4-dichlorophenyl)-2-(1,2,4-triazol-1-yl)-ethan-1-ol as an active compound in the treatment of viral diseases.

It is known that azole derivatives, such as 2-(α-hydroxybenzyl)-benzimidazole -benzimidazole (cf. Burger's Medicinal Chemistry, IV edition, 1979, Part 2, page 554 et seq.; editor M.E. Wolff), and 2-hydroxybutylazoles, such as vibunazole (German Laid-Open Application DOS 3,238,903), as well as other members of this class of substances (German Laid-Open Application DOS 3,315,808) display anti-viral activity. However, the benzimidazoles do not possess in vivo activity, and the other known compounds too, generally have an unsatisfactory action.

To date, the compound of the formula I has only been known to display a fungicidal (European Patent 15,756) and an antimycotic (European Patent 36,153) activity.

It is an object of the present invention to provide a novel antiviral active compound having an improved action.

We have found that this object is achieved and that the compound of the formula I and its physiologically tolerated addition salts with acids surprisingly possess very good antiviral properties which in fact are better than those of the above prior art azole derivatives. The present invention therefore relates to the use of 1-(4-chlorophenyl)-1-(2,4-dichlorophenyl)-2-(1,2,4-triazol-1-yl)-ethan-1-ol (formula I)

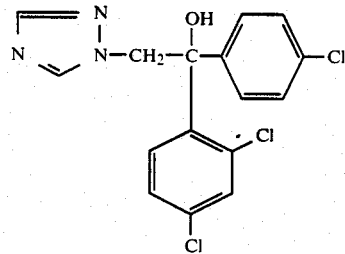

and its physiologically tolerated salts in the preparation of drugs for the treatment of viral diseases.

Among the essential differences between the compound of the formula I and the above azole derivatives whose antiviral activity has already been described are the types of substituents on the carbinol carbon atom. The compound of the formula I can be prepared by the process stated in European Patent 36,153, for example by reacting a compound of the formula II

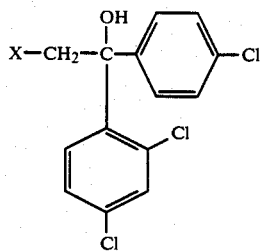

where X is a leaving group capable of being substituted nucleophilically, with 1,2,4-triazole (III)

and, if desired, converting the resulting reaction product into a physiologically tolerated addition salt with an acid.

Conventional acids preferably used for the formation on of physiologically tolerated salts are hydrohalic acids, such as hydrobromic acid and, in particular, hydrochloric acid, with which the novel compound forms a particularly readily crystallizing salt. Other examples are phosphoric acid, nitric acid, sulfuric acid, monofunctional and bifunctional carboxylic acids and hydroxycarboxylic acids, such as acetic acid, maleic acid, succinic acid, fumaric acid, tartaric acid, citric acid, salicylic acid, sorbic acid or lactic acid, and sulfonic acids, such as p-toluenesulfonic acid and naphthalene-1,5-disulfonic acid.

The compound of the formula I contains a chiral center and is obtained in general as a racemate, from which pure enantiomers can be obtained by a conventional method, for example via the diastereomeric salts formed with optically active acids. Both the racemate and the pure enantiomers and mixtures of these are suitable anti-viral agents.

As stated above, the compound of the formula I possesses a powerful antiviral activity, in particular against Herpes viruses. Thus, the novel use of the compound of the formula I constitutes a valuable addition to the possible therapy for viral diseases.

In the Examples below, test methods and the antiviral actions of 1-(4-chlorophenyl)-1-(2,4-dichlorophenyl)-2-(1,2,4-triazol-1-yl)-ethan-1-ol are described. The known compound 2-(4-chlorophenoxymethyl)-3,3-dimethyl-1-(1,2,4-triazol-1-yl)-butan-2-ol (vibunazole) is used as a comparative active compound.

EXAMPLE 1

Cell culture experiments

Herpes Simplex Virus and human cytomegalovirus multiply readily in cultures of monkey kidney cells. The infections are distinguished by characteristic cytopathic effects which occur about 8–12 hours after infection and can easily be observed and assessed. Antiviral properties of test substances which are non-toxic for the host cells or display their action against the infecting viruses in a concentration which is non-toxic for the cells can be readily characterized by the reduction of the cytopathic effect in this system.

The cells used were monkey kidney cells of the strain RC-37 Rita (Italodiagnostics, Rome), which were cultured in basal Eagle's medium (BME; Eagle, H., J. Exp. Med. 102 (1955), 595–601) until infection with the HSV-1 strains ANG (Schröder et al., Intervirology 6 (1976), 270–284) and WAL (Kirchner et al., J. Immunol. 117 (1978), 1753). On infection with the virus, the BME medium was replaced with medium 199 (Morgan et al., Proc. Soc. Exp. Biol., Med. 73 (1950), 1–8). The cells were infected after the formation of an almost confluent lawn with a multiplicity of two infectious virus particles (PFU) per cell. The suspensions of the virus strains had titers of from $2 \times 10^7$ to $1 \times 10^8$ PFU/ml. The test substances were introduced in non-cytotoxic concentration into the medium of the infected cells at various times from 1 hour before to 2 hours after infection. The cytotoxicity limits were tested on the basis of growth curves and the colony-forming ability of isolated cells. The action of the substances was monitored in comparison with control cultures both by microscopic observation and by determining the progeny cell viruses. The virus titer was determined as described by Russell(Nature, London, 195 (1962), 1028–1029).

The compound of the formula I exhibited a very good inhibition of the cytopathic effect, substantially superior to that achieved with the comparative compound at the same concentration. After application of the active compound used according to the invention, the virus titers too were substantially lower than in the case of the comparative compound.

EXAMPLE 2

Testing the antiviral action in the guinea-pig (cutaneous infection model).

These tests were carried out essentially in accordance with the instructions given by Huber et al. (J. Invest. Dermatol. 62 (1974), 92–95).

Guinea-pigs weighing 400–500 g were epilated in the region of the rear flank, anesthetized with nembutal and infected intracutaneously with HSV-1 WAL (about $1 \times 10^5$ to $5 \times 10^5$ PFU/animal) using a Buntscheid multiple-needle gun. The substances to be tested were administered perorally by gavage at various times (from 2 to 48 hours) after infection. The development and healing of virally caused lesions at the points of infection were monitored, and documented photographically.

While administration of the comparative compound had an insignificant effect on the course of the infection compared with untreated controls, the compound of the formula I resulted in less pronounced development and more rapid healing of these virally caused lesions when used in the same dose.

The compound of the formula I is therefore particularly useful for the enteral, parenteral and external treatment of virus infections in humans and animals.

According to studies, examples of indications in human medicine are the following: *Herpes labialis* and *Herpes genitalis*, *Herpes* Zoster (shingles), varicella (chickenpox), *Keratoconjunctivitis herpetica*, infectious mononucleosis and cytomegalovirus infections.

In veterinary medicine, suitable fields of application are pseudorabies virus infections of pigs and cattle, rhinotracheritis virus infections in the horse and Marek's disease in hens.

The compound I can be used alone or together with other known active compounds, in particular antibiotics.

The chemotherapeutic agents or formulations are prepared in a conventional manner, in particular by mixing an appropriate dose with the conventional solid, semisolid or liquid carriers or diluents and the conventional pharmaceutical auxiliaries, in accordance with the desired route of administration (cf. H. Sucker et al., Pharmazeutische Technologie, Thieme-Verlag, Stuttgart, 1978).

Examples of suitable forms for administration are tablets, coated tablets, capsules, pills, suppositories, aqueous solutions, suspensions and emulsions, and where appropriate sterile injectable solutions, non-aqueous emulsions, suspensions and solutions, ointments, creams, pastes, lotions, powders, etc.

The compound I is preferably present in the pharmaceutical formulations in a concentration of from 0.5 to 90% by weight, based on the total mixture.

To achieve the desired results in the case of oral administration either in human or in veterinary medicine, the active compound can be administered in general in amounts of from about 0.1 to about 10.0, preferably from 0.2 to 6, mg/kg of body weight per day, preferably in the form of several single doses. However, it may be necessary to deviate from the stated doses, and to do this as a function of the nature and severity of the disorder, the type of formulation and the route of administration of the drug, as well as the period or interval between administrations. Thus, it may be sufficient in some cases to use less than the abovementioned amount of active compound, while in other cases the above amount of active compound has to be exceeded.

Examples of pharmaceutical formulations:

EXAMPLE A

Tablets containing 250 mg of active compound Composition for 1,000 tablets:

| Compound of the formula I | 250 g |
| --- | --- |
| Potato starch | 100 g |
| Lactose | 50 g |
| Gelatine solution (4% strength) | 45 g |
| Talc | 10 g |

Preparation

The finely powdered active compound, potato starch and lactose are mixed, the mixture is moistened thoroughly with about 45 g of 4% strength gelatine solution and then granulated to give fine particles, and the granules are dried. The dry granules are sieved and then mixed with 10 g of talc, and the mixture is pressed in a rotary tableting machine to give tablets. The tablets are introduced into polypropylene containers which are closed tightly.

EXAMPLE B

Cream containing 1% of active compound

| Compound of the formula I | 1.0 g |
| --- | --- |
| Glycerol monostearate | 10.0 g |
| Cetyl alcohol | 4.0 g |
| Polyethylene glycol-400 stearate | 10.0 g |
| Polyethylene glycol sorbitan monostearate | 10.0 g |
| Propylene glycol | 6.0 g |
| Methyl p-hydroxybenzoate | 0.2 g |
| Deionized water, to make up to | 100.0 g |

Preparation

The very finely powdered active compound is suspended in propylene glycol, and the suspension is stirred into a melt, at 65° C., comprising glycerol monostearate, cetyl alcohol, polyethylene glycol-400 stearate and polyethylene glycol sorbitan monostearate. A solution, at 70° C., of methyl p-hydroxybenzoate in water is emulsified in this mixture, the emulsion is cooled, and the resulting cream is homogenized in a colloid mill and then introduced into tubes.

EXAMPLE C

Powder containing 1% of active compound

| | |
|---|---|
| Compound of the formula I | 1.0 g |
| Zinc oxide | 10.0 g |
| Magnesium oxide | 10.0 g |
| Finely divided silica | 2.5 g |
| Magnesium stearate | 1.0 g |
| Talc | 75.5 g |

Preparation

The active compound is micronized in a jet mill employing air, and is then mixed with the other components to give a homogeneous mixture. This is forced through a sieve of No. 7 mesh size and then introduced into polyethylene containers with a dusting attachment.

We claim:

1. The method of treating DNA viral diseases in a patient suffering therefrom, which comprises administering enterally, parenterally or topically to said patient an effective amount for treating DNA viral diseases of 1-(4-chlorophenyl)-1-(2, 4-dichlorophenyl)-2-(1, 2, 4-triazol-1-yl)-ethan-1-ol (formula I)

* * * * *